United States Patent [19]

Ross

[11] 4,017,736
[45] Apr. 12, 1977

[54] AIR PURIFICATION SYSTEM UTILIZING ULTRAVIOLET RADIATION

[76] Inventor: Henry M. Ross, The Lawn, Nokesville, Va. 22123

[22] Filed: Mar. 24, 1976

[21] Appl. No.: 669,766

Related U.S. Application Data

[63] Continuation-in-part of Ser. No. 509,885, Sept. 27, 1974, abandoned.

[52] U.S. Cl. .............................................. 250/435
[51] Int. Cl. ......................................... G01n 21/24
[58] Field of Search .......... 250/432, 433, 434, 435, 250/436, 437, 438

[56] References Cited

UNITED STATES PATENTS

| 3,757,495 | 9/1973 | Sievers | 250/436 X |
| 3,937,967 | 2/1976 | Steinitz | 250/435 |

Primary Examiner—Davis L. Willis

[57] ABSTRACT

An air purification system utilizes a pre-filter metal mesh and sub-micron laminar flow cell to remove particles and a high intensity ultraviolet generator to kill microorganisms as air is forced by fan means through a shielded enclosure.

1 Claim, 2 Drawing Figures

AIR PURIFICATION SYSTEM UTILIZING ULTRAVIOLET RADIATION

CROSS-REFERENCES TO RELATED APPLICATIONS

The present application is a continuation-in-part of Ser. No. 509,885, "Air Purification System Utilizing Ultraviolet Radiation", filed Sept. 27, 1974 by Henry M. Ross and now abandoned.

BACKGROUND OF THE INVENTION

The invention relates to air purification equipment which is designed to remove airborne particulate material and at the same time kill airborne microorganisms, including viruses.

Modern techniques and standards in operations involving food handling and the manufacture of many products require a clean air environment. Elaborate and expensive equipment is available to produce clean air, but the cost and inconvenience of installation is prohibitive in many instances where the demand for cleanliness is the greatest. The efficiency and effectiveness of the available equipment leaves much to be desired and discourages use where the equipment might otherwise be employed.

It is particularly important in food handling enviroments to reduce airborne microorganisms. Contamination and spoilage of meats and other perishable food products cause large wastage and produce consumer dissatisfaction. The reduction of airborne microorganisms and maintenance at acceptable levels extends the shelflife of perishable products and assures the consumer of a quality product.

Bacteria which produce food spoilage and disease are typically no larger than 1/50,000 of an inch. A cubic inch of space would hold 10 trillion medium-sized bacteria, or as many as there are stars in 100,000 galaxies. Cocci range from 0.4 micron to 2 microns in diameter. The smallest bacillus is approximately 0.5 micron in length and 0.2 in diameter. The largest pathogenic bacilli are seldom greater than 1 micron in diameter and 3 microns in length. The average diameter and length of pathogenic bacilli are 0.5 micron and 2 microns, respectively. Different species of bacteria vary in size, and there is some variation within a species, but, as a rule, the size of each species is fairly constant.

SUMMARY OF THE INVENTION

In accordance with the invention there is provided an air purification system which may be either portable or stationary in operation. An elongated hollow metallic enclosure contains a two-stage mechanical filter comprising a metallic mesh pre-filter and a sub-micron laminar flow cell of fiberglass and paper capable of removing microorganisms down to 0.3 micron in size. A high intensity ultraviolet generator is mounted within the enclosure, and air is drawn through the filter and past the ultraviolet generator by means of a fan. The enclosure is constructed to provide complete shielding for the ultraviolet generator.

DESCRIPTION OF THE PREFERRED EMBODIMENT

Figure 1:
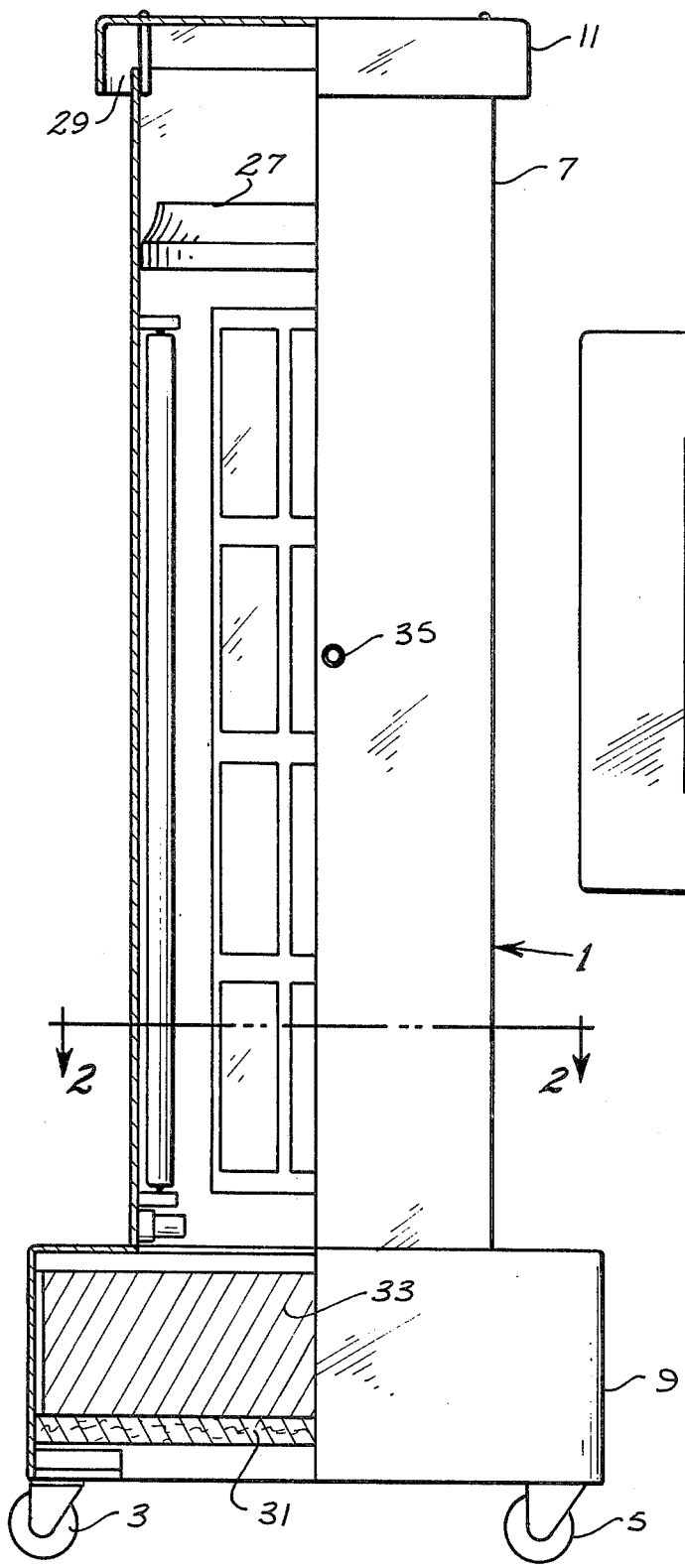
FIG. 1 is an elevation view in partial section of a portable system constructed in accordance with the invention.
Figure 2:
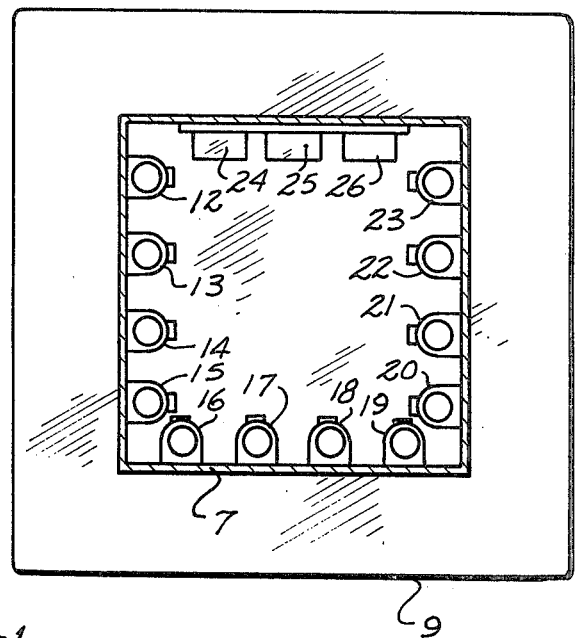
FIG. 2 is a cross-sectional view taken along line 2—2 of FIG. 1.

The invention will be readily understood by referring to FIG. 1 which shows a portable unit 1 designed to roll about on casters such as shown at 3 and 5. An upstanding metallic enclosure 7 includes a base 9 and cap member 11. A plurality of ultraviolet tubes 12–23 are mounted vertically on three walls of the enclosure, and tube ballasts 24–26 are mounted on the fourth wall.

A fan 27 is positioned within the enclosure 7 to draw air upward from the base 9 past the ultraviolet tubes 12–23 and out the top of the unit through air gap 29 extending around the periphery of enclosure 7. As the air enters the base 9 it passes first through a metallic mesh pre-filter 31 and then through a sub-micron laminar flow cell 33 which is constructed of fiberglass and paper.

In operation the unit is positioned within the air in which clean air is desired. The portable unit typically requires between 500 and 600 watts of electrical power and can be safely operated from a standard appliance receptacle outlet. A conventional electrical appliance cord (not shown) is attached to the unit 1 for connection to a standard duplex receptacle. The unit is controlled by a switch (not shown) mounted on the outer enclosure.

When electrical power is applied to the unit, the fan draws air from floor level upward through the metallic mesh prefilter 31 which removes large airborne particles. The air then passes through the sub-micron laminar flow cell which removes smaller particles down to 0.3 micron in size. After having substantially all of the particulate material removed, the air passes through an area subjected to intense ultraviolet radiation emitted by ultraviolet tubes 12–23. The radiation is completely contained within metallic enclosure 7 and kills in a single pass any airborne microorganisms which may have passed through the sub-micron laminar flow cell, an accomplishment not attained by any known commercially available equipment. A peephole 35 with an optical filter to prevent eye damage is provided in enclosure 7 to enable inspection of the ultraviolet tubes and insure that they are all operating. The system does not produce ozone.

What is claimed is:

1. A portable air purification system utilizing ultraviolet radiation comprising
   an upstanding elongated metallic enclosure having a lower inlet and an upper outlet for the passage of air,
   fan means mounted within said enclosure between the inlet and outlet to cause the movement of air therebetween,
   a metallic cap member mounted over said outlet,
      said cap member having downturned edges spaced from said elongated enclosure to form an air passageway directing the flow of air downwardly,
   a base member comprising a hollow metallic enclosure mounted on casters, said base member being joined to said upstanding enclosure at the inlet end thereof,
   filter means positioned within said base member to remove particles of impurities contained in the air passing therethrough,
      said filter means comprising a metallic mesh pre-filter and a sub-micron laminar flow cell, said sub-micron laminar flow cell being constructed of fiberglass and paper with a porosity sufficiently small to cause particles with diameters larger than 0.3 microns to be trapped by said flow cell, a plurality of high intensity ultraviolet tubes vertically mounted within said enclosure in position to expose all air passing therethrough to ultraviolet radiation, a peep-hole provided with optical filter means positioned in said elongated enclosure to enable inspection of said ultraviolet tubes while in operation, whereby straight-line air flow is maintained with particulate materials being removed from the air by the filter means and microorganisms being killed by ultraviolet radiation to produce a clean air environment with complete suppression of ultraviolet radiation.

* * * * *